United States Patent [19]

Farr et al.

[11] 4,245,656
[45] Jan. 20, 1981

[54] OBSTETRIC GLOVES

[76] Inventors: Larry D. Farr, G2010 Beckman Ct., Flint, Mich. 48504; Anthony G. Fabaz, 2104 Painted Post Dr., Flushing, Mich. 48433

[21] Appl. No.: 12,207

[22] Filed: Feb. 14, 1979

[51] Int. Cl.³ .............................................. A61B 5/10
[52] U.S. Cl. ................................. 128/775; 128/778; 128/361; 33/174 D; 2/160
[58] Field of Search ............ 128/775, 778, 361; 33/174 D; 2/159, 160

[56] References Cited

U.S. PATENT DOCUMENTS

| | | | |
|---|---|---|---|
| 2,394,140 | 2/1946 | Biscow | 128/361 |
| 2,847,676 | 8/1958 | Scott | 2/159 |
| 2,924,220 | 2/1960 | Von Micsky | 128/778 X |
| 3,097,637 | 7/1963 | Horton | 128/775 |
| 3,126,890 | 3/1964 | Deming | 128/361 |
| 3,643,651 | 2/1972 | Cuadros | 128/778 |
| 4,141,345 | 2/1979 | Allen et al. | 128/778 |

FOREIGN PATENT DOCUMENTS

| | | | |
|---|---|---|---|
| 297501 | 7/1932 | Italy | 128/361 |
| 11910 | of 1897 | United Kingdom | 128/361 |

*Primary Examiner*—Kyle L. Howell
*Attorney, Agent, or Firm*—Basile, Weintraub & Hanlon

[57] ABSTRACT

A device to permit a medical practitioner to perform internal measurements of patients without the insertion of measurement instruments. Finger enclosures adapted to be worn over two fingers or incorporated into two fingers of conventional examination gloves are equipped with a measuring tape, associated with a first enclosure, a free end thereof extending through the first enclosure and secured to a second enclosure such that by separating the two enclosed fingers, a length of tape equal to the distance between the fingers is drawn from the first enclosure.

10 Claims, 4 Drawing Figures

OBSTETRIC GLOVES

BACKGROUND OF THE INVENTION

A. Field of the Invention

The present invention pertains to medical measurement equipment. More particularly, the present invention pertains to internal measurement devices. Even more particularly, the present invention pertains to surgical finger enclosures and gloves equipped with means for making internal measurements.

B. BACKGROUND OF THE INVENTION

It is well known to those skilled in the medical and particularly the gynecological and obstetric arts that the dimensions of organs, accessable by pelvic or vaginal examination may be of great relevance in evaluating the condition of the patient.

Such interior measurements are particularly important during labor and delivery wherein the rate and degree of dilation of the cervix provide critical information to the physician as to the progress and normalcy of the delivery. Therefore, vaginal and pelvic examinations are normally carried out several times during a normal delivery.

However, it is also well known that even under the most scrupulously sterile conditions, a vaginal examination will result in the introduction of bacteria to the uterus. It is therefore desirable that such examinations be performed efficiently in order to limit their number and duration.

As the rate as well as the extent of dilation is a factor in evaluating the progress of labor, accurate measurement of the cervix is desired. Such measurements during labor and delivery are often approximated by the physician who manually or visually estimates the dimensions of the cervical opening. Measurement instruments for measuring the dilation of the uterus are also known. However, during labor, the introduction of bacteria by the examination, as well as the inconvenience and discomfort caused the patient by the examination dictate that such examinations are best done simply and quickly and, in so far as possible, with minimal use of measurement equipment.

Thus, great benefits would be realized by incorporating into a standard surgical examination glove, or into finger enclosures compatible therewith, measurement means whereby the dimensions of interior, anatomical parts, and, in particular, measurements of the dilation of the cervix, could be effected quickly and without the introduction of obtrusive measurement instruments.

Thus, an object of the present invention is to provide a means for simplifying and increasing the accuracy of internal measurements, particularly that of the dilation of the uterus during labor.

A further object of the present invention is to provide examination finger enclosures or gloves with means whereby accurate measurements of internal, anatomical parts may be effected without the introduction of measurement instruments and equipment.

Prior Art Statement

U.S. Pat. Nos. 2,847,676, 2,555,203, and 3,740,262 comprise the most pertinent prior art of which Applicant is aware.

SUMMARY OF THE INVENTION

In accordance with the present invention, a device for performing internal examinations of patients, and, particularly, for making internal measurements is provided which comprises finger enclosures which may be used with or incorporated into examination gloves of conventional construction. The device is equipped with a measurement device by means of which a medical practitioner may ascertain the dimensions of internal portions by movement of the enclosed fingers.

In accordance with the present invention, a measurement tape is associated with a first finger enclosure, generally covering the middle finger and retained in a contained position against a restricted opening, a free end of the tape being drawn therethrough. The protruding end of the measurement tape is anchored to a second finger enclosure, generally covering the index finger. In this manner, when the first and second fingers are moved apart, the measurement tape is drawn through the restricted opening of the first finger enclosure. Thus, the length of tape drawn and extending between the fingers will be equal to the distance between the fingers. The relationship between the tape and the restricted opening is such that the tape will not pass through the opening unless pulled; thus, the length of tape pulled from the first finger is not altered when the fingers are brought together, and remains, hence, an accurate measurement of the distance through which the fingers had been separated.

Thus, by means of the present invention, it is possible to determine the dimenions of internal anatomical parts by enclosing two fingers in the first and second finger enclosures hereof, inserting those fingers into the body, parting the fingers to conform to the dimension of the part to be measured, and then removing the fingers. In this manner, the dimension of that part will be equal to the length of tape extending between the fingers, which can be determined easily by conventional methods, such as by measurement against a ruler.

For a more complete understanding of the present invention, reference is made to the following detailed description and accompanying drawing. In the drawing like reference characters refer to like parts throughout the several views in which:

BRIEF DESCRIPTIONS OF THE DRAWINGS

DESCRIPTION OF THE PREFERRED EMBODIMENT

Figure 1:
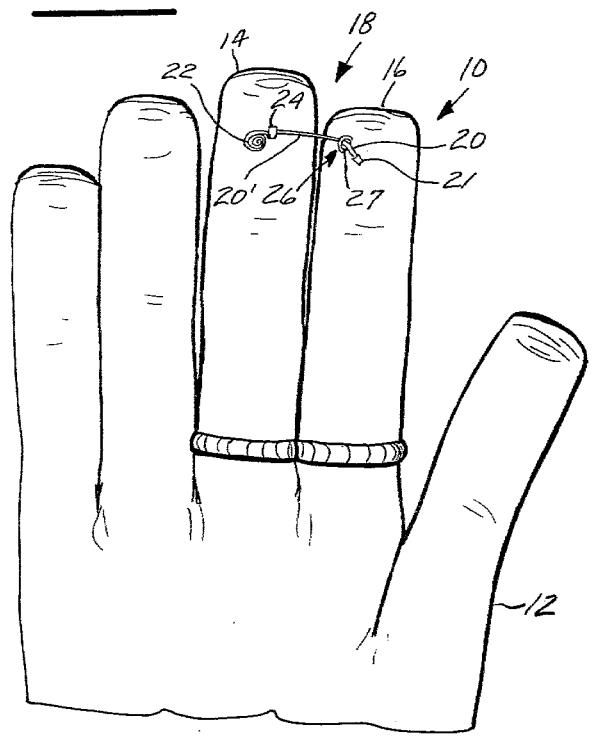
FIG. 1 is a front view of the examination and measurement device of the present invention, depicted in combination with a conventional examination glove.

Now, with reference to the drawing and in particular to FIG. 1, there is depicted the examination and measurement device of the present invention, indicated generally at 10. The device 10 is shown in combination with a surgical glove 12 which is of conventional construction, having five finger portions. The device 10 comprises at least two hollow finger enclosures, 14, 16 and is preferably constructed from a flexible, durable, material which conforms readily to the fingers of the wearer, providing a snug fit, and which is capable of withstanding sterilization procedures.

The device 10 is equipped with measurement means, indicated generally at 18, which enable a medical practitioner to take an accurate measurement of internal, anatomical parts using only fingers and without introducing any additional measurement instruments.

The measurement means, 18, comprises generally a measurement tape, 20, which is coupled with the first finger enclosure, generally worn on the middle finger of the practitioner and which is preferably wound into a coil 22.

The tape, 20, may comprise a simple length of surgical thread, or may be provided with markings at measured intervals to enable the physician to determine the length of the tape extended directly without the use of other measurement devices.

The tape 20, as noted, is coupled with the first finger enclosure 14 and, in a preferred embodiment, wound into a coil 22 which is carried thereon as best seen in FIG. 1. The coil 22 is contained behind a restricted opening 24 carried on the first finger enclosure 14, a free end of the tape 20 protruding therethrough.

The restricted opening 24 may comprise a hook or an eye and is of a predetermined size such that the coil (22) tape cannot pass through the opening, but that the tape 20, when uncoiled, may be drawn therethrough.

The protruding end 21 of the tape 20 is anchored to a second finger enclosure 16 preferrably worn on the index finger. The second finger enclosure 16 is provided with an achoring point 26 through which the protruding end 21 of the tape 20 is secured. This securement of the tape 20 to the second finger enclosure may be accomplished during the manufacturing process either externally of the enclosure 16, as shown in FIG. 1 or within it as in FIG. 4. As shown in FIG. 1, the second finger enclosure 16 may be provided with an exterior eye 27 to which the free end 21 of the tape 20 is secured. The tape 20 may be secured to the eye 27 by tying or by providing the end of the tape 20 with a knot larger than the opening of the eye 27 to prevent its being pulled therethrough.

Figure 4:
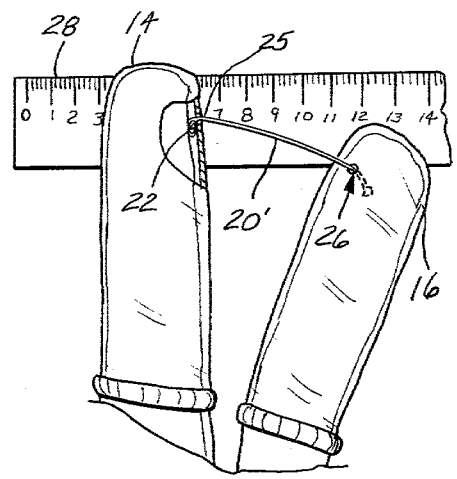
FIG. 4 is a sectional view of an alternate construction of the first embodiment of the measurement device hereof.
Figure 3:
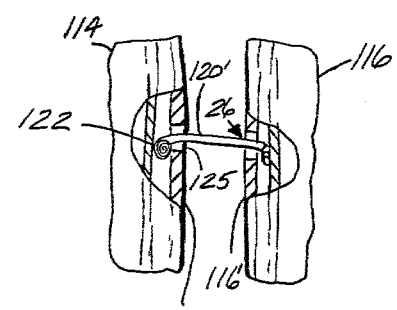
FIG. 3 is a partial sectional view of an alternate construction of the second embodiment of the present invention.

In alternate embodiments the free end 21 of the tape 20 may be secured to the second finger enclosure 16 by inserting it into the enclosure 16 and securing it therein with a knot or by equivalent means shown in FIG. 4.

It is to be understood that prior to use, the protruding end 21 drawn from the coil of tape 22 is relatively short such that the tape 20' extending between the two finger enclosures 14, 16 will be taut even when the enclosures 14, 16 are abutting. In this manner, the coil 22 is normally retained tightly against the restricted opening 24.

In use, the coil 22 of tape 20 is held tightly against the restricted opening 24. However, when the finger enclosures 14, 16 are drawn apart, The tape 20 is pulled from its coil 22 and drawn through the restricted opening 24. The balance of the tape 20 remains in its coil 22 and is thereby prevented from passing through the restricted opening 24. As there are no recoiling or retration means, the tape 20 drawn from the coil 22 remains uncoiled and slack between the finger enclosures 14, 16. Thus, the length of slack tape 20 extending between the finger enclosures 14, 16 provides a measurement of the distance to which the enclosures 14, 16 had been separated.

In an alternate embodiment illustrated in FIG. 4, the coil 22 of tape 20 may be deployed within the first finger enclosure 14, adjacent an aperture 25 which defines a restricted opening. In this embodiment, the coil 22 is lodged between the finger and the enclosure, the tape 20 being withdrawn from the coil and through the aperture 25 by the separation of the finger enclosures.

Figure 2:
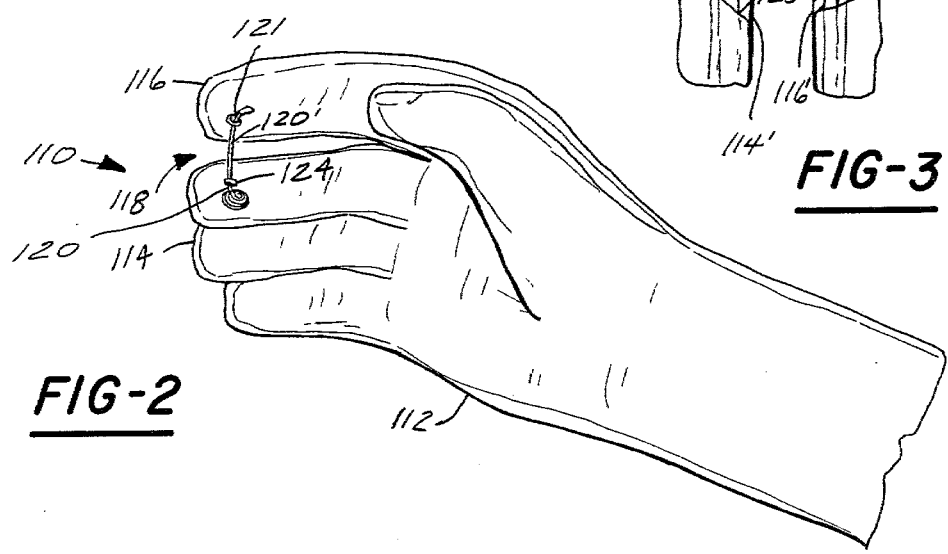
FIG. 2 is a front elevational view of a second embodiment of the measurement device thereof, incorporated into an examination glove.

Now, and with reference to FIG. 2 there is depicted a second embodiment of the measuring device hereof, wherein the device depicted generally at 110 is incorporated into an examining glove 112 of conventional construction having at least first and second finger portions 114, 116 respectively. Preferably, the first finger portion 114 is that which is worn over the middle finger, and the second finger portion, 116, over the index finger of the examiner.

The measurement means 118 comprises a measurement tape 120, which is preferably wound into a coil 122 coupled with the first finger portion 114 of the glove 112. As in the first embodiment, the tape 120 may comprise simply a length of surgical thread or may be provided with spaced markings to permit direct determination of the extended length thereof.

The measurement tape 120 is preferably coiled and contained behind a restricted opening 124 carried on the first finger portion 114 of the glove, a free end 121 of the tape protruding through a restricted opening 124 provided thereon. As in the first embodiment, the restricted opening 124 may comprise a hook or an eye and is of a predetermined size large enough to acommodate the tape 120 but too small to allow the coil 122 to pass therethrough.

As in the first embodiment, the protruding end of tape drawn from the coil 122 is relatively short such that the tape 120' extending between the two glove fingers 114, 116 will be taut and the coil 122 held tightly against the restricted opening 124, even when the glove fingers 114, 116 are abutting. Thus, when the tape 120 is pulled by the separation of a glove fingers 114, 116, the tape 120 is drawn from its coil 122 and through the restricted opening 124. The balance of the tape 120 remains in its coil 122 and is thereby prevented from passing through the restricted opening 124. As there are no retraction or recoiling means, the tape 120 drawn remains as slack between the two fingers 114, 116.

In an alternate method of constructions, the coil 122 of tape 120 may be deployed within the glove finger 114, and retained behind a restricted opening 125. In this embodiment, it is preferrable that the aperture 125 through which the tape 120 issues not expose the finger of the examiner to the atmosphere, breaking sterility.

As illustrated in FIG. 4, such exposure may be prevented by providing the glove fingers 114, 116 housing the device 10 with outer walls 116', 114', such that the enclosure of the hand is in all respects complete and there are no apertures through which bacteria may escape from the practitioner's hand to the surface. In this manner, the wall of the glove covering the fingers is continuous, the apertures being provided only in the outer walls 114', 116' and the free end 121 of the tape 120 extending through only the outer wall 116' and being secured between the two walls 116, 116'. Thus, it is to be appreciated that the measuring tape 120 is deployed between the inner and outer walls of the fingers and sterile conditions are preserved.

The methods of practicing both embodiments of the present invention are identical. When it is desired to determine the length of an internal organ or member, such as the cervix during a delivery, the two fingers within the enclosures between which the measuring tape 20 (120) is deployed are inserted into the patent's body, during labor into the vaginal opening, according to conventional, accepted procedure. The internal member, particularly the cervix may then be measured by placing the fingers having the measurement device associated therewith along the member (cervix) and by then parting the fingers such that one finger rests at each end of the member (cervix) along the dimension to be measured. As the fingers are parted, the tape 20 (120) is pulled from its coil 22 (122) through the restricted opening 24 (124) of the first finger enclosure 14 (114), the balance of the tape 20 (120) remaining in its coil 22 (122) behind the opening 24 (124). As a result of this separation of the fingers, a slack of tape indicated at 20' (120') extending between the finger enclosures 14, 16 (114, 116) will be equal to the distance by which the fingers were separated when within the body of the patient, that is, equal to the length of the anatomical portion measured. Thus, the fingers 14, 16 (114, 116) may be brought together after the anatomical portion has been measured, and withdrawn from the body without altering the length of tape 20' (120') drawn, preserving the measurement of that portion. Outside the body, the length of the extracted measuring tape may be determined, directly, if marked, or by comparison with a conventional measurement device 28 such as a ruler. (FIG. 4).

In this manner, the measurement of internal members and organs may be taken by an examiner using only fingers, quickly and safely and without the danger or discomfort imposed on the patient by the insertion of measurement instruments.

It is to be understood that many adaptations of the method employed herein are possible without departing from the spirit or scope of the present invention.

Having thus described the invention, what is claimed is:

1. A device to permit a medical practitioner to perform internal measurements on a patient, comprising:
   (a) a flexible covering for enclosing each of two fingers of the practitioner, said device being deployed between two of the fingers; and
   (b) a measuring tape contained behind a restricted opening associated with a first finger enclosure having a free end extending therethrough, said free end being secured to a second finger enclosure, said tape being coiled and said coil being carried on said first finger enclosure, retained behind said opening and wherein said opening comprises an eye which is smaller than the coil of tape but sufficiently larger to permit the drawn tape to pass therethrough;
   whereby separation by the practitioner of said two enclosed fingers causes a length of tape equal to the distance between the fingers to be drawn from behind said restricted opening to provide a measurement of an internal, anatomical part where the enclosed fingers are inserted into the patient and separated to conform to the dimensions of that internal part.

2. The device of claim 1 wherein the covering comprises two finger pieces, adapted to be worn over surgical gloves, constructed from a resilient, durable material.

3. The device of claim 2 wherein the tape is coiled within said first enclosure and is drawn from the coil as the tape is pulled by the separation of the fingers, said opening in said first enclosure being smaller than the coil of tape, but sufficiently large to permit the drawn tape to pass therethrough.

4. The device of claim 2 wherein the free end of the tape is secured within said second finger enclosure.

5. The device of claim 1 wherein the covering is a full, conventional, surgical glove, comprising an enclosure for each of five fingers, the device being deployed between two of the fingers.

6. The device of claim 5 wherein the tape is coiled within said first enclosure and is drawn from the coil as the tape is pulled by the separation of the fingers, said opening in said first enclosure being smaller than the coil of tape, but sufficiently large to permit the drawn tape to pass therethrough.

7. The device of claim 5 wherein the free end of the tape is secured within said second finger enclosure.

8. The device of claim 2 or 5 wherein a free end of the tape is secured within an eye provided on the second finger enclosure.

9. A device to permit a medical practitioner to perform internal measurements on a patient, comprising:
   (a) a covering for enclosing at least a portion of each of two fingers of the practitioner, wherein:
      1. said covering is a full, conventional surgical glove which comprises an enclosure for each of five fingers.
      2. said device is deployed between two of said fingers; and
   (b) a measuring tape contained behind a restricted opening associated with a first finger enclosure having a free end extending therethrough, said free end being secured to a second finger enclosure, wherein:
      1. said first finger enclosure is provided with an inner and outer wall, said measuring tape being contained therebetween, and
      2. said measuring tape is coiled within said first enclosure and is drawn from the coil as the tape is pulled by the separation of the fingers, said opening in said first enclosure being smaller than the coil of tape but being sufficiently large as to permit the drawn tape to pass therethrough;
   whereby separation by the practitioner of the two enclosed fingers causes a length of tape equal to the distance between the fingers to be drawn from behind said restricted opening to provide a measurement of an internal, anatomical part where the enclosed fingers are inserted into the patient and separated to conform to the dimensions of that internal part.

10. The device of claim 9, wherein said second finger enclosure is provided with an inner and an outer wall and the free end of said measurement tape is secured between the inner and outer walls of said second finger enclosure.

* * * * *